United States Patent
Kenney et al.

(10) Patent No.: US 10,870,822 B2
(45) Date of Patent: Dec. 22, 2020

(54) VESSEL FOR GROWTH OF BIOLOGICAL ENTITIES

(71) Applicant: CORNING INCORPORATED, Corning, NY (US)

(72) Inventors: David Alan Kenney, Greenville, NH (US); Nikolaos Pantelis Kladias, Horseheads, NY (US); Shang-Pin Kwei, Boston, MA (US); Aravind Raghavan Rammohan, Big Flats, NY (US); Joseph Christopher Wall, Southborogh, MA (US); Kathy Marie Youngbear, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 39 days.

(21) Appl. No.: 15/304,313

(22) PCT Filed: Apr. 9, 2015

(86) PCT No.: PCT/US2015/025069
§ 371 (c)(1),
(2) Date: Oct. 14, 2016

(87) PCT Pub. No.: WO2015/160614
PCT Pub. Date: Oct. 22, 2015

(65) Prior Publication Data
US 2017/0037350 A1    Feb. 9, 2017

Related U.S. Application Data

(60) Provisional application No. 62/120,566, filed on Feb. 25, 2015, provisional application No. 61/980,673, filed on Apr. 17, 2014.

(51) Int. Cl.
*C12M 3/00* (2006.01)
*C12M 1/00* (2006.01)
(Continued)

(52) U.S. Cl.
CPC .......... *C12M 23/08* (2013.01); *B01F 9/0021* (2013.01); *B01F 15/00876* (2013.01); *C12M 27/20* (2013.01); *B01F 2009/0092* (2013.01)

(58) Field of Classification Search
CPC .................................. C12M 23/08; B01L 3/08
See application file for complete search history.

(56) References Cited

U.S. PATENT DOCUMENTS 3,718,229 A * 2/1973 Wyeth .................. B65D 1/0276
215/373
4,665,035 A    5/1987 Tunac
(Continued)

FOREIGN PATENT DOCUMENTS

CN    202246687 U    5/2012
CN    202576417 U    12/2012
(Continued)

OTHER PUBLICATIONS

Maier, U. et al.; "Characterisation of the gas-liquid mass transfer in shaking bioreactors." Biochemical Engineering Journal, vol. 7, Issue 2, pp. 99-106, Mar. 2001.
(Continued)

*Primary Examiner* — Nathan A Bowers
(74) *Attorney, Agent, or Firm* — F. Brock Riggs

(57) ABSTRACT

A 5-liter bioreactor vessel enables a substantial increase in the volume of biological media that can be cultivated in the vessel compared to conventional designs. Moreover, when agitated at 1.5× the shaking frequency of a conventional 3-liter bioreactor (i.e., 90 rpm versus 60 rpm), the 5-liter vessel achieves a 19% increase in cell aeration without exceeding the maximum shear stress limit for cell viability. The 5-liter vessel optionally includes a plurality of internal
(Continued)

baffles configured to disrupt the liquid vortex and reduce the maximum shear stress transferred to biomedia contained within the vessel.

12 Claims, 22 Drawing Sheets

(51) Int. Cl.
*C12M 1/24* (2006.01)
*B01F 9/00* (2006.01)
*B01F 15/00* (2006.01)

(56) References Cited

U.S. PATENT DOCUMENTS

| | | | |
|---|---|---|---|
| 5,484,072 A * | 1/1996 | Beck | B65D 1/0284 |
| | | | 215/375 |
| 5,924,583 A | 7/1999 | Stevens et al. | |
| 7,238,345 B1 | 7/2007 | Seid, Jr. et al. | |
| 7,381,559 B2 | 6/2008 | Ellis et al. | |
| 2005/0277188 A1 | 12/2005 | Ellis et al. | |
| 2005/0277191 A1 * | 12/2005 | Ellis | C12M 23/08 |
| | | | 435/404 |
| 2006/0141614 A1 * | 6/2006 | Puskeiler | B01F 3/04531 |
| | | | 435/289.1 |
| 2006/0205065 A1 * | 9/2006 | Bossi | C12M 23/08 |
| | | | 435/304.3 |
| 2007/0128081 A1 * | 6/2007 | Ellis | B01L 3/08 |
| | | | 435/305.1 |
| 2007/0166822 A1 * | 7/2007 | Kenney | C12M 23/08 |
| | | | 435/325 |

FOREIGN PATENT DOCUMENTS

| | | |
|---|---|---|
| JP | 62053815 A | 3/1987 |
| JP | 2013212088 A | 10/2013 |

OTHER PUBLICATIONS

Weheliye, W. et al.; "PIV Measurements in a Shaken Cylindrical Bioreactor." 16th Int. Symp. on Application of Laser Technologies to Fluid Mechanics, Lisbon, Portugal, Jul. 2012.
Tianzhong L. et al.; "Numerical Simulation of Flow in Erienmeyer Shaken Flask." Computational Fluid Dynamics, Book edited by Hyoung Woo, ISBN 978-953-7619-89-6, Chapter 7, pp. 157-172, Jan. 2010.
Zhang, H et al.; "Computational-fluid dynamics (CFD) analysis of mixing and gas-liquid mass transfer in shake flasks." Biotechnology and Applied Biochemistry, vol. 41, Issue 1, pp. 1-8, Feb. 2005.
English Translation of JP2016562533 Office Action dated Mar. 6, 2019; 5 Pages; Japanese Patent Office.
Japanese Aptent Application No. 2016562533; Machine Translation of the Office Action dated Jan. 15, 2020; Japan Patent Office; 5 Pgs.

* cited by examiner

D: flask diameter
$D_0$: shaking diameter
$\omega$: angular velocity of shaker

FIG. 4A
60 rpm
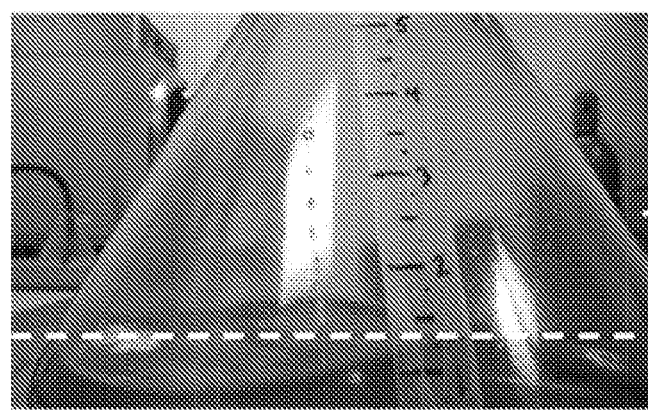
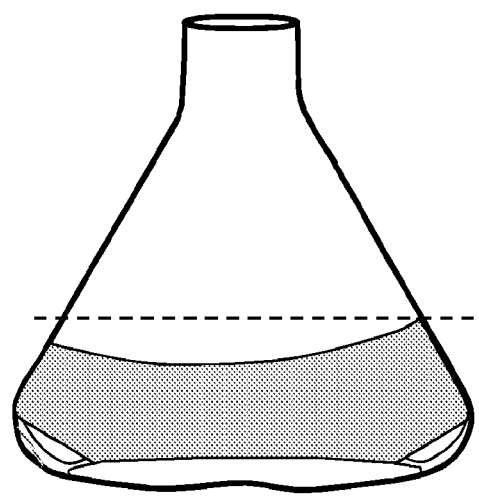

FIG. 4B
120 rpm
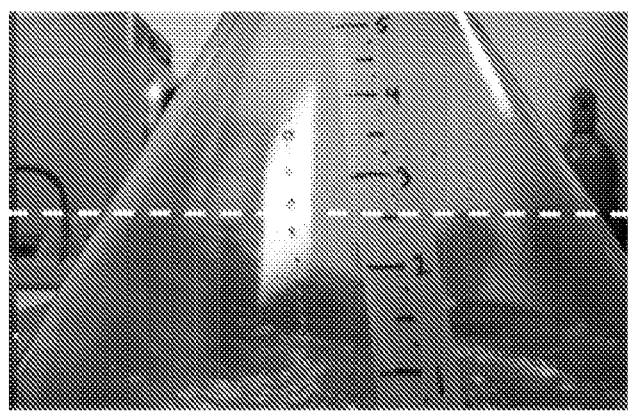
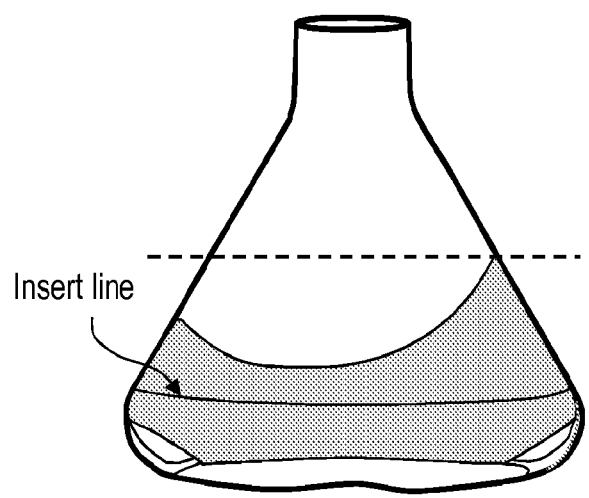
Insert line

FIG. 4C
240 rpm
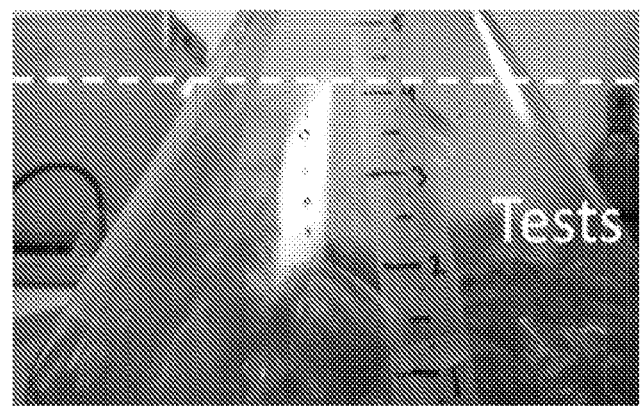
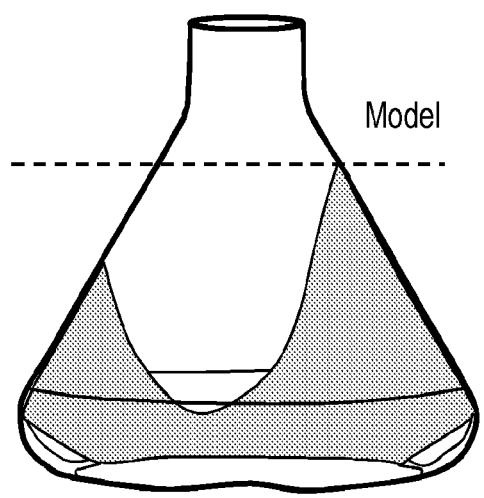
Model

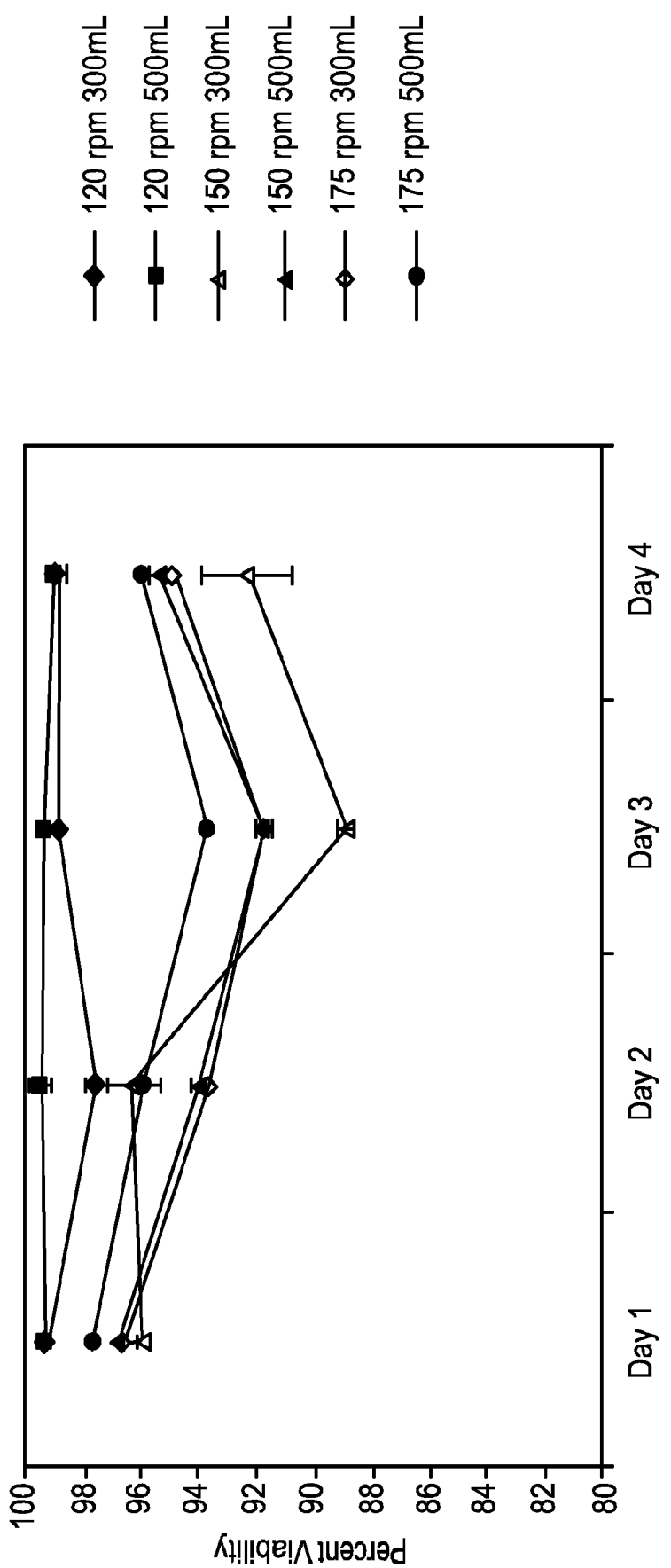

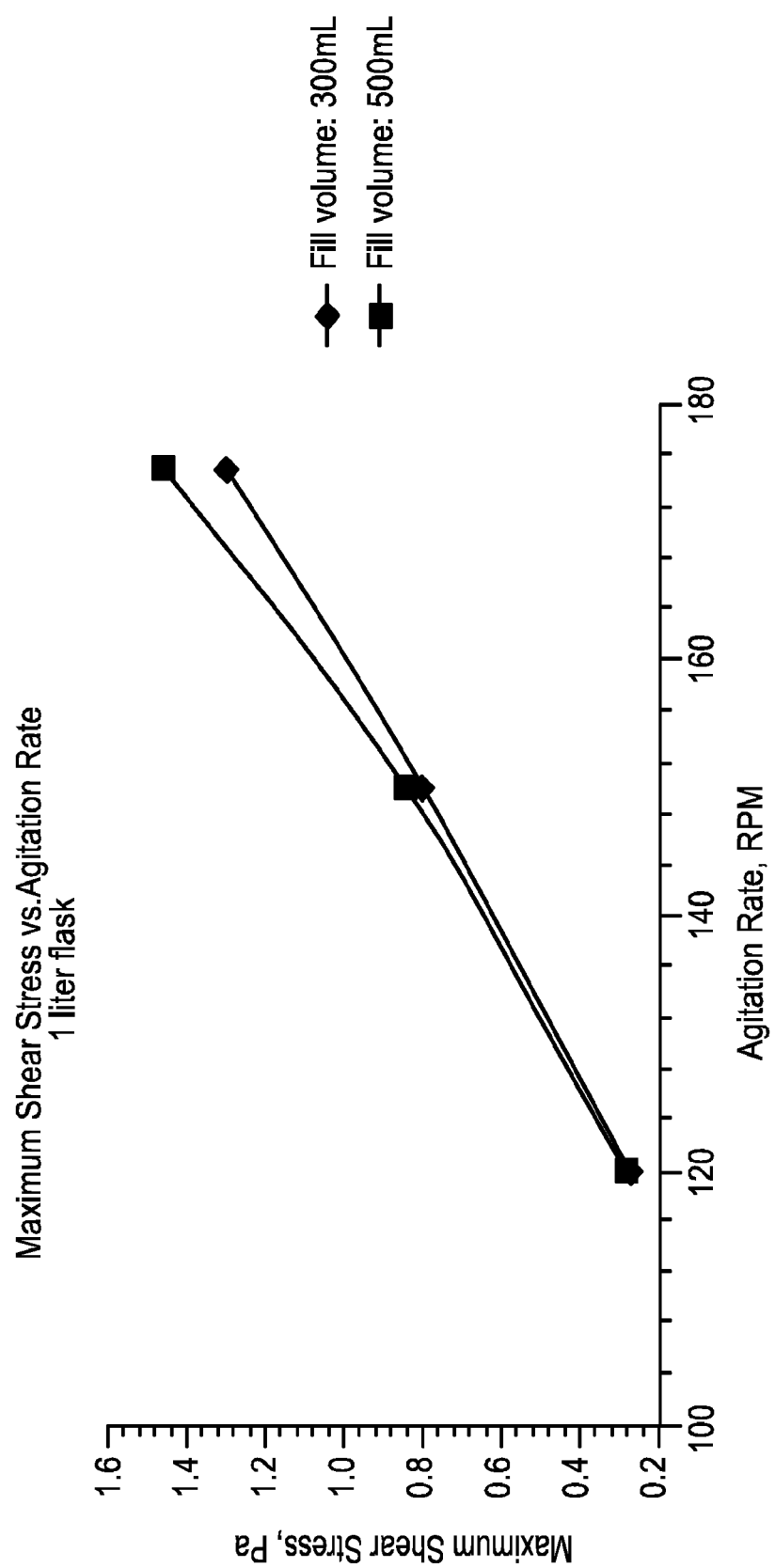

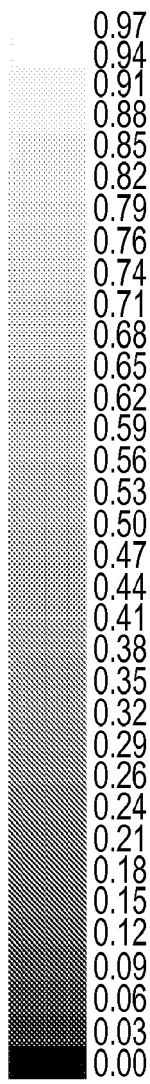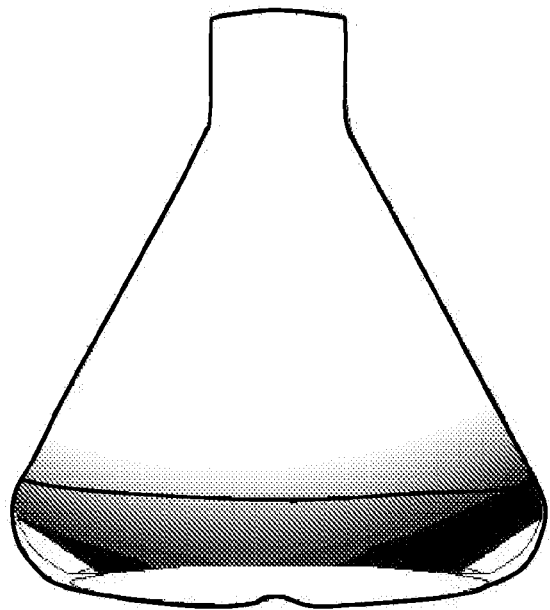
FIG. 8A
3 liter non-baffled

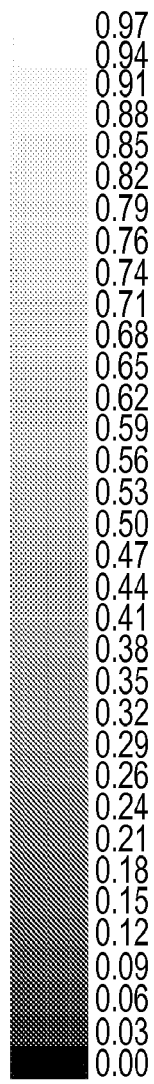
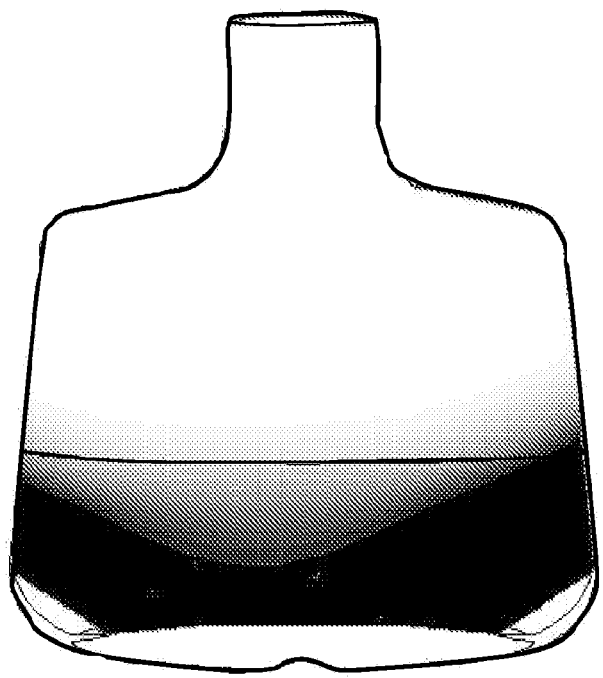
FIG. 8B
5 liter non-baffled

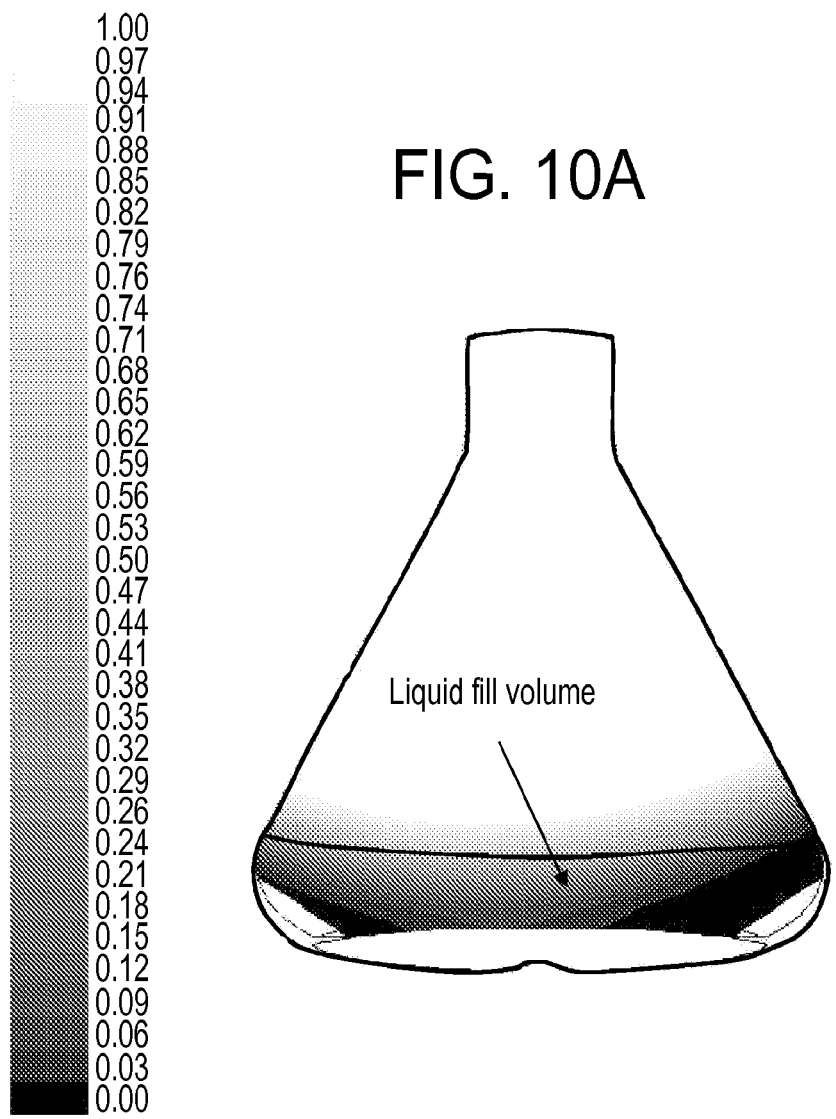

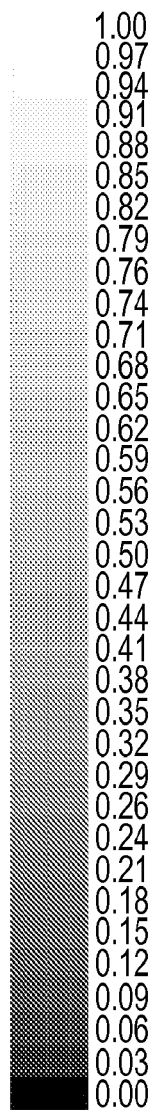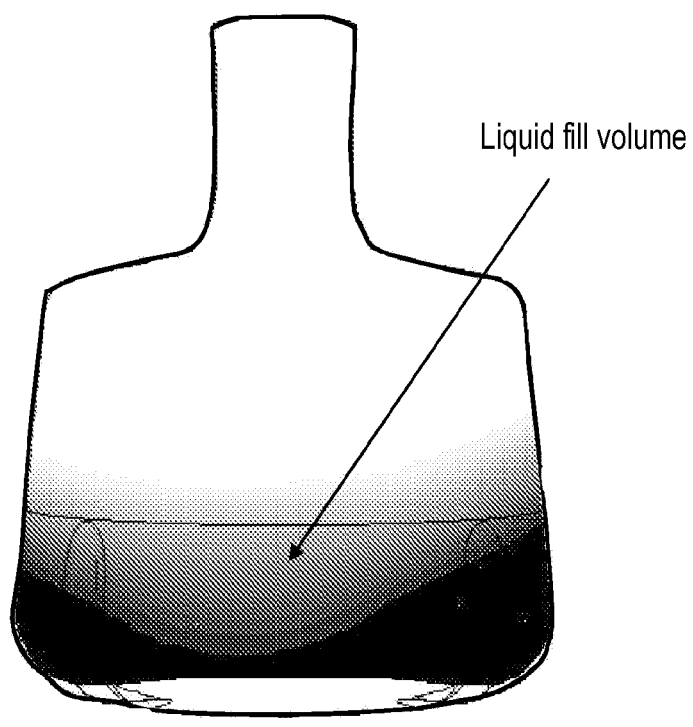
FIG. 13A

Wall Contact angle: 30°

Wall Contact angle: 90°

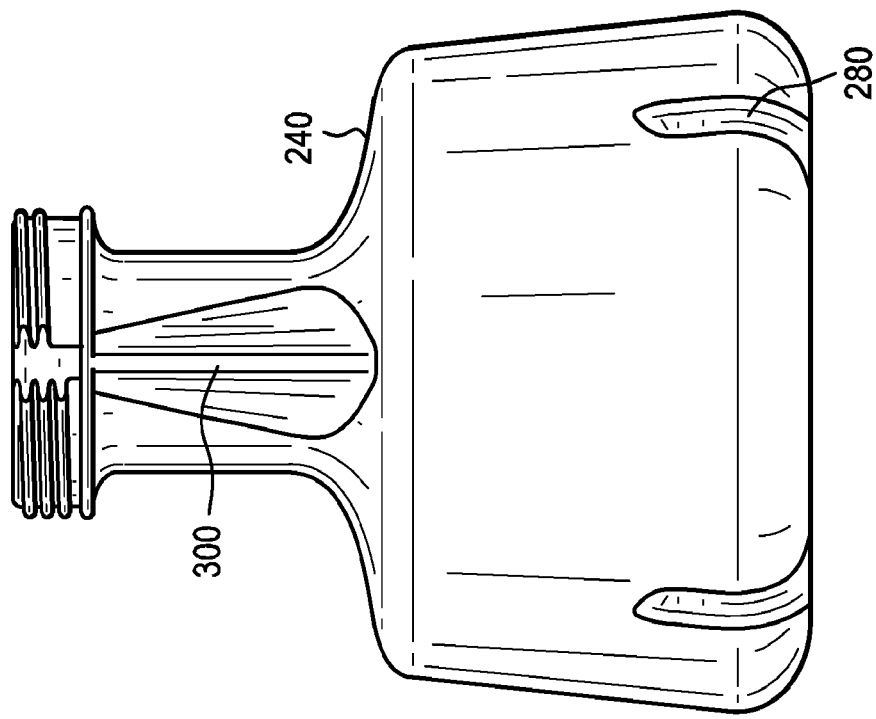
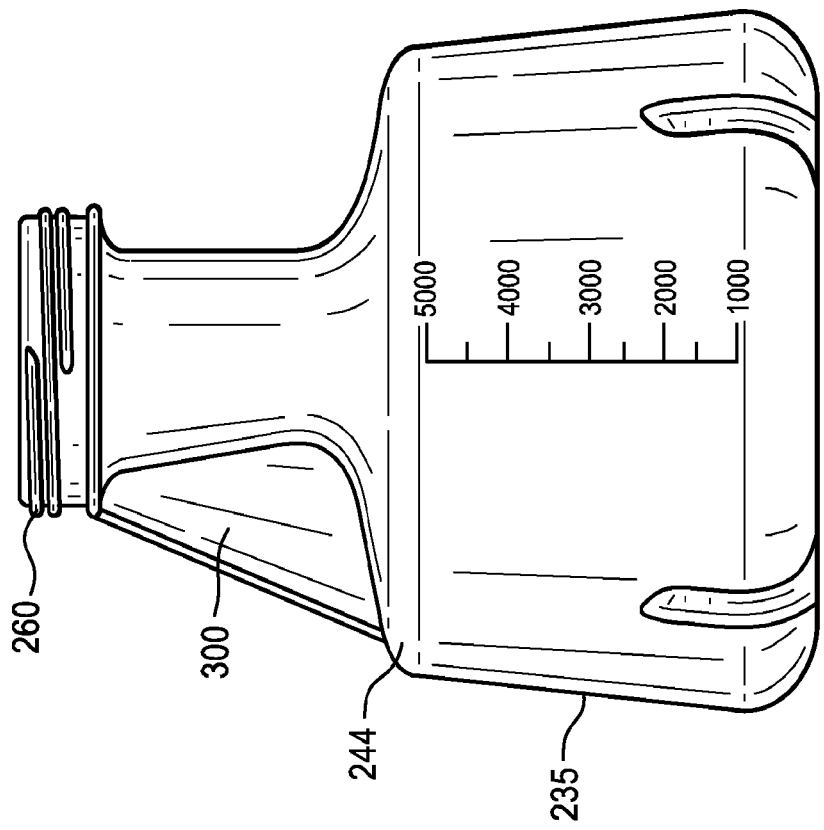

VESSEL FOR GROWTH OF BIOLOGICAL ENTITIES

CROSS-REFERENCE TO RELATED APPLICATIONS

This application claims the benefit of priority under 35 U.S.C. § 365 of International Application No. PCT/US15/25069, filed on Apr. 9, 2015, which claims the benefit of priority under 35 U.S.C. § 119 of U.S. Provisional Application Ser. No. 62/120,566 filed on Feb. 25, 2015 which also claims the benefit of priority under 35 U.S.C. § 119 of U.S. Provisional Application Ser. No. 61/980,673 filed on Apr. 17, 2014 the content of which is relied upon and incorporated herein by reference in its entirety.

BACKGROUND

Field

The present disclosure relates generally to laboratory ware, and more specifically to cell culture vessels and related systems, components and methods.

Technical Background

Biological entities such as bacteria, yeast, fungi and animal/plant cells are commonly cultured in vitro in various types of containers or flasks. The cells or their by-products are used in assorted disciplines related to biotechnology, including medicine, pharmacology, and genetic research and engineering.

One method of cultivating biological entities involves placing them in a vessel partially filled with a culture medium and agitating the vessel, e.g., using an orbital shaker while exposing the culture medium to a source of oxygen. An illustration of the shaking mechanism is depicted in FIG. 1. Vessel 100 is placed on a shaker table 200, which performs a circular motion with a radius equal to half the shaking diameter.

The growth of microorganisms in such a vessel is dependent on adequate access of the culture medium 60 to oxygen. For media contained in vessels, oxygen is transferred into the media culture via the vessel's head space 120. Because oxygen diffusion across the gas-liquid interface is proportional to the surface area of the liquid, the larger the liquid surface area, the better the biomedia aeration. Shaking of the vessel, for example, creates a vortex that exposes more liquid surface area to the head space.

The oxygen transfer rate (OTR) between the head space 120 and the liquid phase may be described as OTR=$k_L\alpha$ ($C^*_L - C_L$), where $k_L\alpha$ is the volumetric mass transfer coefficient, $C^*_L$ is the oxygen concentration in the saturated gas-liquid interface, and $C_L$ is the oxygen concentration in the liquid phase.

The volumetric mass transfer coefficient, $k_L\alpha$, is a function of the geometry of the vessel, the process conditions (e.g., shaking frequency and fill volume), as well as the properties of the biological media. An empirical relationship for $k_L\alpha$ may be represented as $k_L\alpha = c_1 d^{1.92} n^{1.16} d_o^{0.38} V_L^{-0.83}$, where d is the maximum inner vessel diameter, n is the shaking frequency, $d_o$ is the shaking diameter, and $V_L$ is the fill volume.

From this empirical relationship, Applicants have shown that comparable cell aeration during scale-up of a vessel of given capacity can be achieved by one or more of (i) an increase to the vessel diameter, (ii) an increase to the shaking frequency, and (iii) an increase to the shaking diameter. If the vessel diameter and the shaking diameter are constrained to remain unchanged, the principle approach to achieve similar aeration in a scaled-up vessel is to increase the shaking frequency. However, with an increase to the shaking frequency, cells experience higher hydrodynamic (shear) stress, which can be detrimental to cell viability if the stress exceeds a maximum limit value.

Accordingly, there exists a need for high-throughput (high volume) cell culture vessels that can be used to culture media without the adverse effects of hydrodynamic stress, and which are compatible with existing infrastructure.

BRIEF SUMMARY

In accordance with embodiments of the present disclosure, disclosed is a scaled-up bioreactor vessel. The vessel has a liquid volume in excess of 3-liters (e.g., 4 or 5 liters) and, to achieve compatibility with existing infrastructure, maintains the same maximum vessel diameter, vessel height, and shaking diameter as a smaller, 3-liter bioreactor vessel. The capacity of a 5-liter vessel is 67% greater than the capacity of a 3-liter vessel.

By way of example, a 5-liter vessel as disclosed herein filled with 2.5-liters of biological media achieves aeration comparable to a 3-liter vessel filled to 1.5 liters at the same shaking frequency. Moreover, the 5-liter vessel exceeds the aeration of a 3-liter vessel at 1.5× the shaking frequency by 19% without exceeding the maximum allowable shear stress for cell viability. The disclosed vessels optionally include a plurality of interior baffles that disrupt the liquid vortex and reduce the maximum shear stress transferred to biomedia contained within the vessel. Each baffle is raised (i.e., convex) with respect to an inner surface of the vessel.

In various embodiments, a vessel for culturing cells comprises a vessel main body defined by a bottom having rounded edges that is integral with a conically-shaped sidewall that tapers inward to a top surface. The vessel further includes an integral elongate annular neck extending upwardly from the top surface to a vessel opening. In contrast to conventional flasks, the sidewall is tapered inward with an inclination angle of 4-10°.

A method of cultivating cells using such a vessel comprises introducing a culture medium into the vessel, introducing at least one selected cell line into the vessel, and agitating the vessel, e.g., at a frequency of greater than 60 rpm.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 4 is a series of modeled drawings and corresponding photographs showing liquid crawl along the sidewalls of a vessel as a function of agitation frequency;

FIG. 6 is a graph showing the effect of shear stress on cell viability;

FIG. 7 is a plot of maximum shear stress versus agitation frequency;

FIG. 8 is a modeled illustration of air volume fraction contours in (a) a 3-liter non-baffled vessel and (b) a 5-liter non-baffled vessel;

FIGS. 13A and 13B are modeled illustrations of air volume fraction contours in example 5-liter vessels;

FIGS. 17A and 17B are perspective drawings of a 5-liter baffled vessel having a V-shaped pour trough.

DETAILED DESCRIPTION

Figure 1:
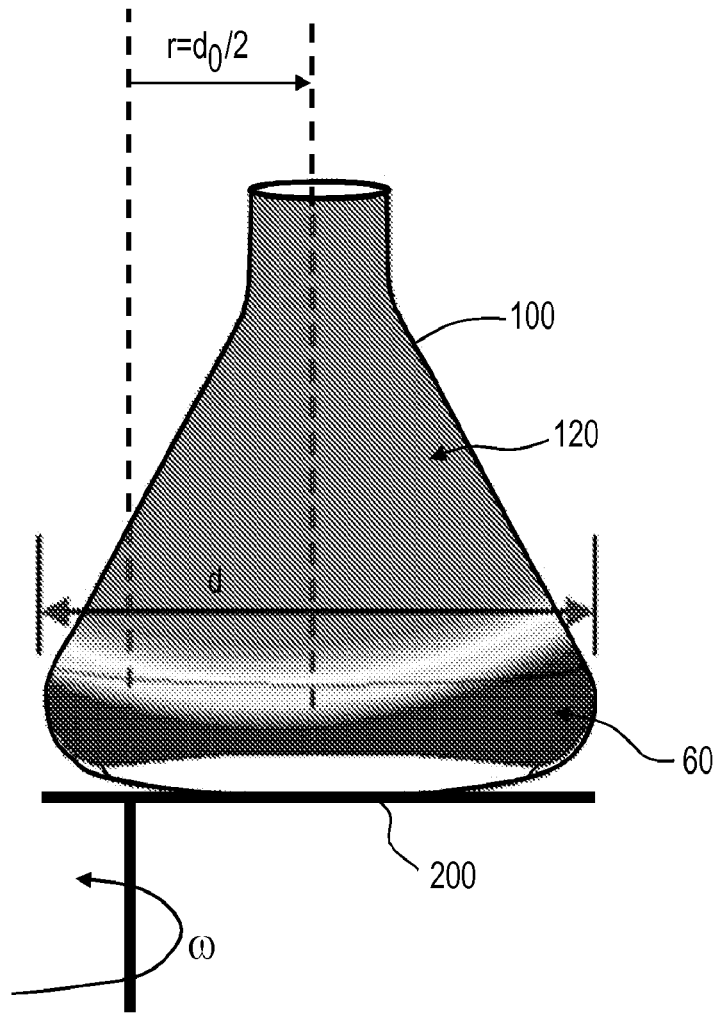
FIG. 1 is a schematic diagram of a vessel subjected to orbital agitation.

Reference will now be made in greater detail to various embodiments of the subject matter of the present disclosure, some embodiments of which are illustrated in the accompanying drawings. The same reference numerals will be used throughout the drawings to refer to the same or similar parts.

Figure 2A:
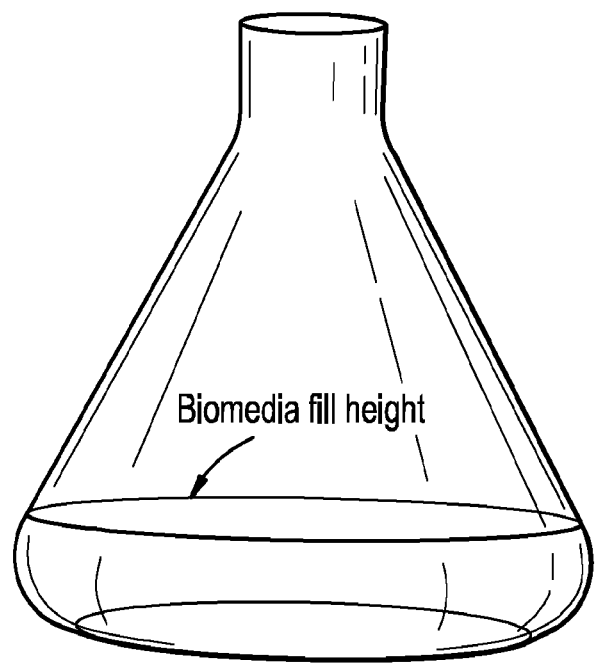
FIG. 2A is a schematic illustration of a conventional 3-liter vessel and FIG. 2B is a schematic illustration of a scaled-up 5-liter vessel with baffles.
Figure 2B:
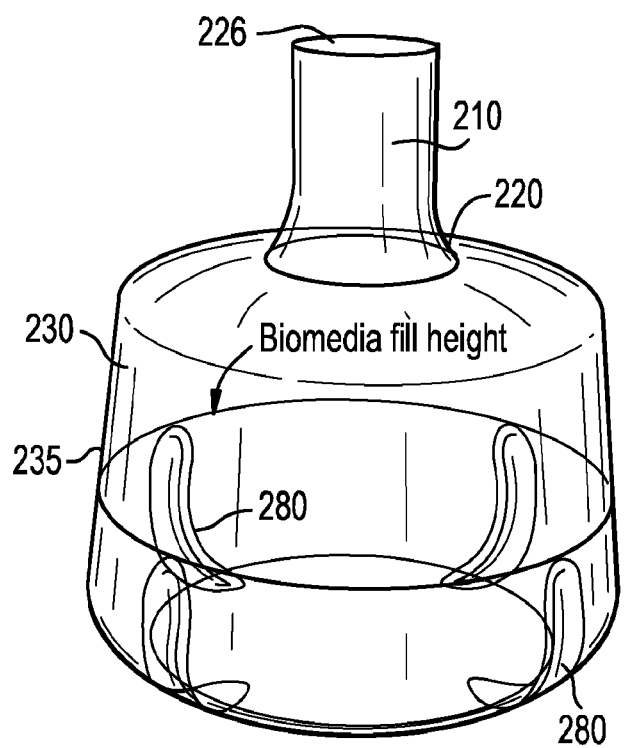

FIG. 2 is a schematic drawing of a conventional 3-liter un-baffled vessel (FIG. 2a) and, as disclosed according to various embodiments herein, a 5-liter scaled-up vessel with baffles (FIG. 2b). Both vessels have a bottom with rounded peripheral edges that are integral with a conically-shaped sidewall that tapers inward.

The walls of the 5-liter vessel are slightly tapered inward with an inclination angle of 4-10° (e.g., 4°, 6°, 8°, or 10°) from the vertical axis, in contrast to the 3-liter vessel where the wall inclination angle is 30°. The less inclined walls of the 5-liter vessel result in an increased volume capacity without any change to the maximum vessel diameter or its overall height. A short, inward tapered transition area 220 joins a neck 210 to the vessel main body 230. In the example of the 3-liter vessel, the neck has a diameter that is about 25% of the maximum vessel diameter. In the example of the 5-liter vessel, the neck has a diameter that is about 33% of the maximum vessel diameter.

Cell culture media and cells may be introduced into the vessel and removed from the vessel through an opening 226. The opening 226 of the vessel may be resealable by way of a cap (not shown) that can be removably attached to prevent contents of the vessel from spilling. The cap may include an open face that is covered by a sheet of filter material. The filter material allows oxygen to enter the vessel interior while reducing the risk of contamination of its contents.

In embodiments, the maximum external diameter of the 5-liter vessel may range from about 220 to 240 mm, e.g., about 220, 230 or 240 mm. An external diameter of the vessel main body 230 may range from a minimum at the tapered end, adjacent the neck, of about 180 to 220 mm to a maximum equal to the maximum external diameter of the vessel. The external diameter of the neck 210 may range from about 60 to 80 mm, e.g. about 60, 70 or 80 mm. The height of the neck 210 may range from about 50 to 80 mm, e.g., about 50, 60 70 or 80 mm. A total height of the vessel may range from about 280 to 290 mm, e.g., about 285 mm. An exterior portion of the neck 210 may be knurled or otherwise roughened to provide a gripping surface. In embodiments, the neck flairs to a vessel opening 226 having a larger cross-sectional area than the neck. For example, the vessel opening 226 may have a diameter ranging from about 90 to 100 mm. A larger opening presents a larger cross-sectional area for improved ventilation.

With reference to FIG. 2b, illustrated are four symmetrically-spaced baffles 280 each having a V-shape, a sidewall angle of 80°-110° and, in embodiments, a height measured parallel to the longitudinal (vertical) axis that is below the 2.5 liter fill height. In embodiments, the baffle height is between 60% to 120% of the height of the 2.5 liter fill level. The baffles run along the vessel sidewall 235 and, where the vessel bottom meets the sidewall, extend radially inward toward the vessel axis. The degree to which the baffle extends inward into the bottom wall of the vessel can be measured by the angle formed between the baffle wall and the bottom wall of the vessel. In the illustrated embodiment the angle is 15°, though the baffle wall-bottom wall angle may range from 5°-30°.

Figure 3A:
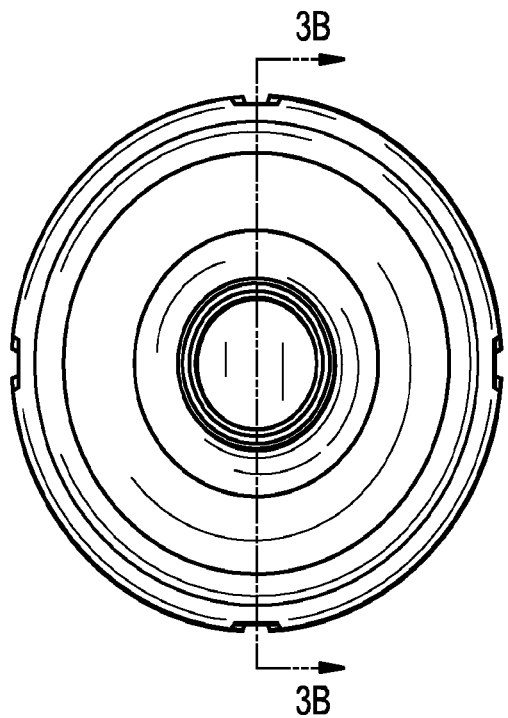
FIG. 3 is a drawing showing various perspectives of a scaled-up 5-liter vessel with baffles.
Figure 3B:
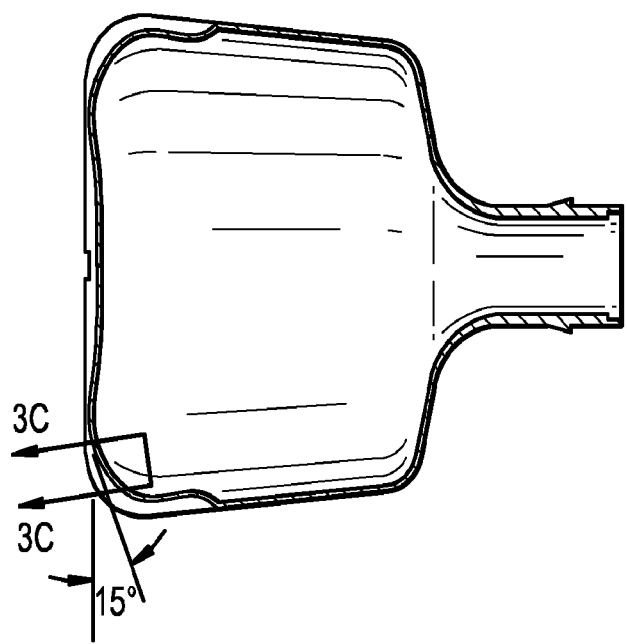
Figure 3C:
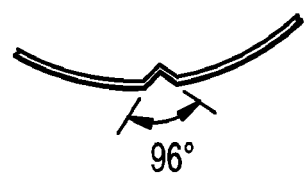

FIG. 3 shows perspective engineering drawings of a scaled-up 5-liter vessel with baffles according to embodiments. In the cross-sectional view (A-A) the baffles define a 15° pitch with respect to the bottom of the vessel. Each baffle height is 1.96 inches (~49.7 mm) over which height each baffle has a depth is 0.23 inches (~5.9 mm). The baffles terminate with a sloping section having a radius of curvature of 1.04 inches (~26.5 mm). Further baffles features are visible in section B-B, including an internal radius of curvature of 0.11 inches (~2.8 mm), an external radius of curvature of 0.44 inches (~11.2 mm), and a V-shaped cross-section, which forms an angle of 96°.

In use, the baffles 280 break the vortex of a stirred liquid and promote growth of biological material. The 5-liter bioreactor baffles are designed to achieve aeration similar to that achieved with the 3-liter bioreactor at the same shaking frequency, or improved aeration at 1.5× the shaking frequency without exceeding the maximum allowable shear stress for cell viability.

The 5-liter vessel design is based on Computational Fluid Dynamics (CFD) analysis of the two-phase flow (air and liquid biomedia) within the shaken vessel. CFD was used to develop a numerical model of the shaken vessel. The model was used to obtain information about aeration, maximum shear stress and degree of mixing. Based on benchmark data for the 3-liter vessel design, CFD analysis was used to design a 5-liter vessel so as to meet or exceed the 3-liter vessel performance.

Based on the empirical relationship discussed above, it was appreciated that in order to achieve comparable cell aeration for an increased fill volume, an increase would need to be made to one or more of the vessel maximum diameter, the shaking diameter and the shaking frequency. Specifically, by way of example, to scale-up the fill volume from 1.5 liters (3-liter vessel) to 2.5 liters (5-liter vessel), from the equation above, it would be necessary to (a) increase the maximum vessel diameter by about 25%, or (b) increase the shaking diameter by about 300%, and/or (c) increase the shaking frequency by about 45%.

In order to produce a vessel this is compatible with existing infrastructure, the maximum vessel diameter and the shaking diameter should remain unchanged with respect to the 3-liter design. Recognizing that 3-liter vessels are typically agitated at a frequency of 60 rpm, in order to achieve the same aeration in a 5-liter vessel, an agitation frequency of about 90 rpm is required. As is discussed below, however, the agitation of a non-baffled, 5-liter vessel would likely produce shear stresses that exceed the maximum allowable stresses for cell viability.

In embodiments, via the placement of baffles in the 5-liter vessel design, the 5-liter vessel filled to 2.5 liters performs comparably to the 3-liter vessel filled to 1.5 liters at 60 rpm, and exceeds the 3-liter vessel performance at 90 rpm without exceeding the maximum allowable shear stress for cell viability at either shaking frequency.

The CFD model was initially validated using the 3-liter vessel design. In experiments, a 3-liter vessel containing colored water was placed on a shaker table and orbitally-agitated at various agitation frequencies (e.g., 60, 120 and 200 rpm) with a shaking diameter of 40 mm. The centrifugal force resulting from the orbital rotation of the vessel pushes the liquid up the sidewalls of the vessel and the free surface of the liquid assumes a concave shape. Liquid displacement up the sidewall increases with agitation frequency and the concomitant increase in centrifugal force. Photographs and modeled results of the liquid crawl are shown in FIG. 4.

Figure 5:
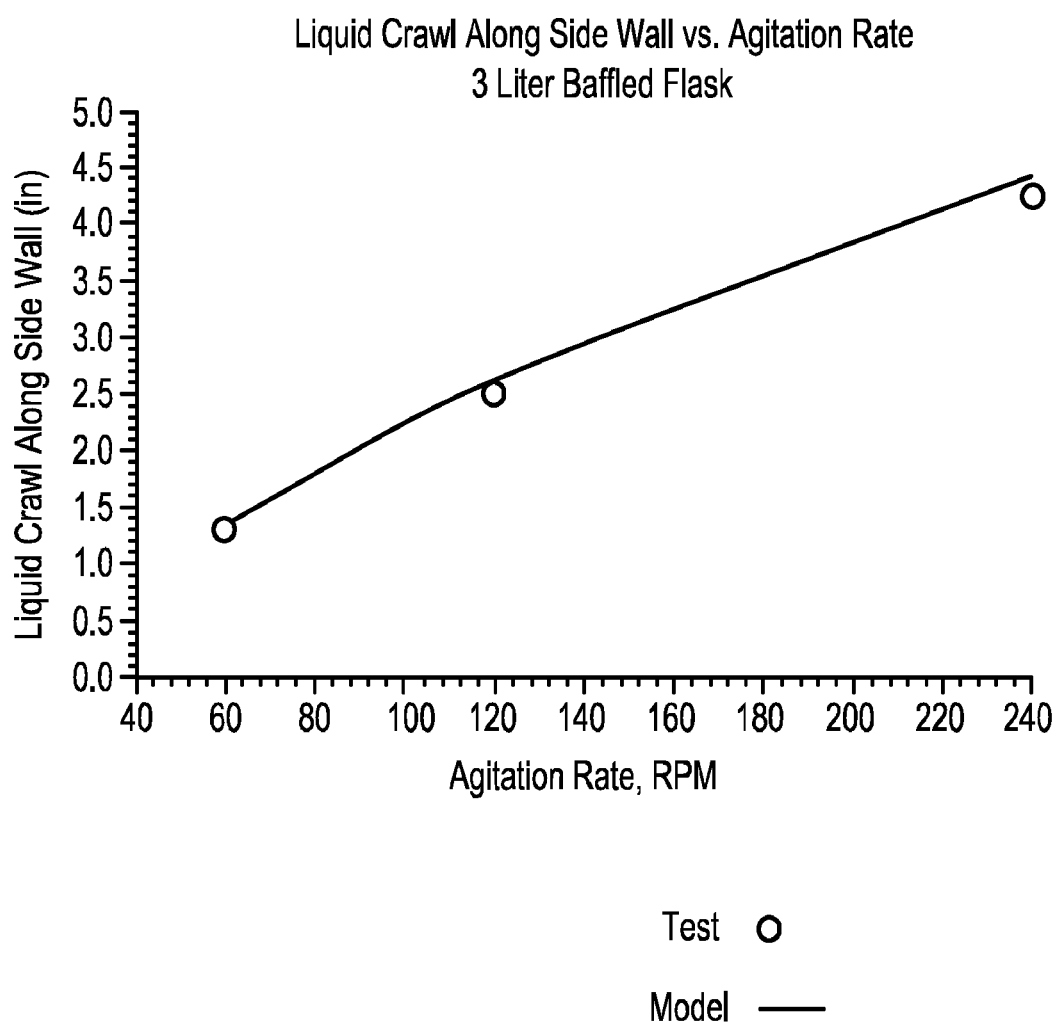
FIG. 5 is a plot of liquid crawl versus agitation frequency for modeled and experimental results.

The model-predicted liquid crawl along the vessel sidewalls was in excellent agreement with the experimental measurements. A direct comparison of the measured versus modeled liquid crawl is shown graphically in FIG. 5. The datum for the measurement of the liquid crawl summarized in FIG. 5 was the insert line depicted by the arrow in FIG. 4, which is located 3 cm above the vessel bottom.

In addition to the liquid crawl tests, cell viability measurements were performed to set a benchmark for the maximum shear stress that can be allowed before there is an effect on cell viability. Cell viability measurements were performed with Sf9 cells. The tests were performed using a 1-liter vessel agitated at 120, 150 and 175 rpm. Two sets of tests were performed at each agitation frequency: one with the vessel filled to 300 mL and one with the vessel filled to 500 mL.

Results of the cell viability measurements are presented in FIG. 6, which shows that the cells are adversely affected at agitation frequencies of 150 rpm and greater, while cell viability is not affected when the 1-liter bioreactor is shaken at 120 rpm.

A CFD model of the 1-liter bioreactor was used to correlate the measured cell viability to the maximum allowable shear stress. The CFD model data were used to calculate the maximum shear stress under the various experimental agitation rates and fill volumes. The results of the CFD model are presented in FIG. 7, which shows that the maximum shear stress at 120 rpm is 0.28 Pa, which is correlated to the maximum shear stress allowed for cell viability.

Figure 9A:
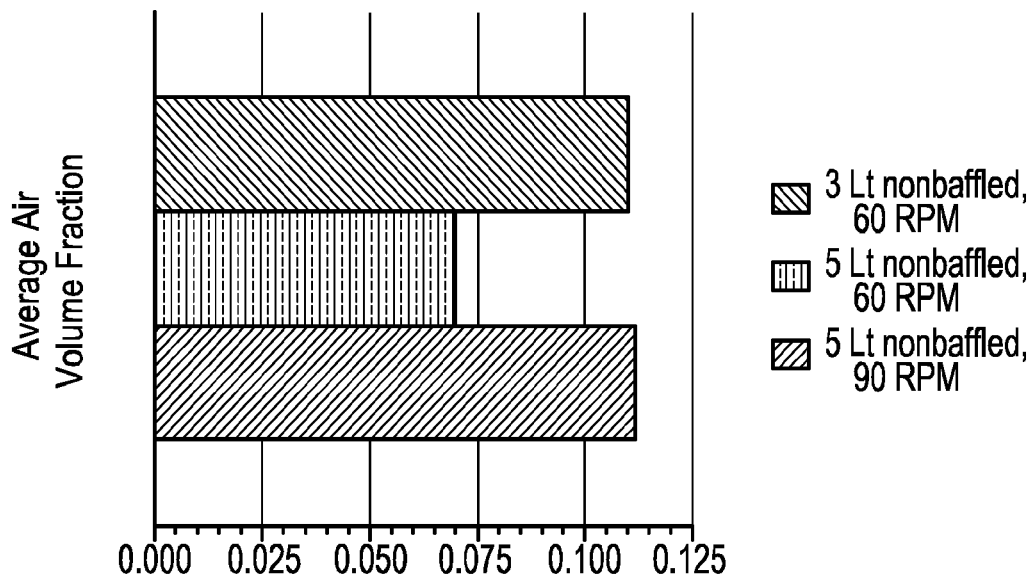
FIG. 9 is a graph comparing (a) aeration and (b) maximum shear stress in 3-liter and 5-liter non-baffled vessels.
Figure 9B:
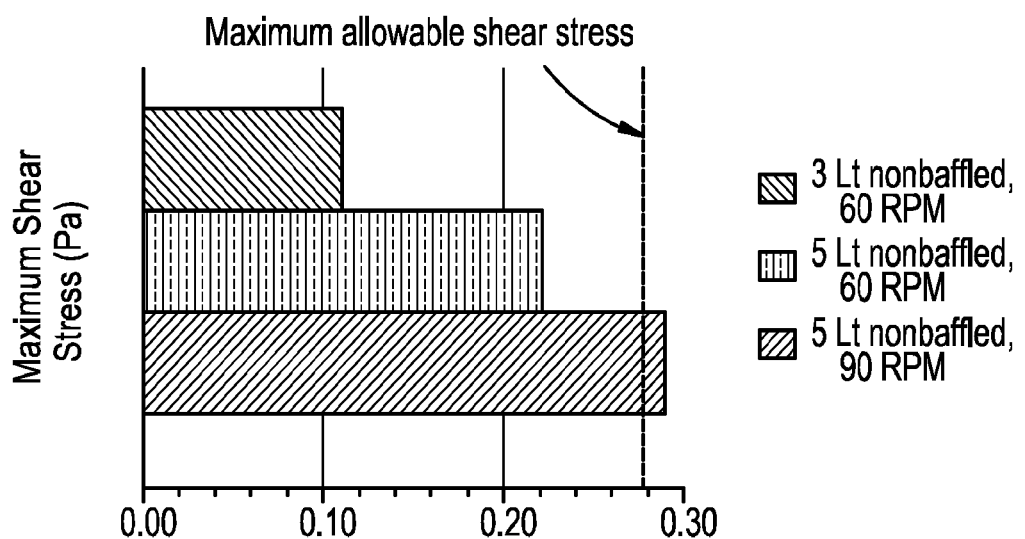

Shown in FIG. 8 are contours of the air volume fraction in the 3-liter non-baffled vessel, as well as in the 5-liter vessel when agitated at 60 rpm. As the liquid is pushed to the vessel sidewalls, within the central region of the vessel air entrains into the volume that is filled with liquid while the vessel is at rest. The average air volume fraction in the fill volume is provided in FIG. 9*a* for the 3-liter and 5-liter scaled-up non-baffled vessels. FIG. 9*a* shows that the 5-liter non-baffled vessel provides 36% less aeration to the cells than the 3-liter counterpart when agitated at 60 rpm. Referring to FIG. 9*b*, at 60 rpm the maximum shear stress in the 5-liter non-baffled vessel is approximately 2× the maximum shear stress in the 3-liter non-baffled vessel.

Referring back to FIG. 9*a*, it can be seen that when the 5-liter non-baffled vessel is agitated at 90 rpm, cell aeration is similar to the 3-liter vessel agitated at 60 rpm. However, as seen in FIG. 9*b*, the maximum shear stress in the 5-liter non-baffled vessel (at 90 rpm) is 0.29 Pa (FIG. 9*b*), which exceeds the maximum allowable shear stress for cell viability.

The introduction of baffles into the 5-liter vessel can disrupt the liquid vortex and reduce the maximum shear stress. In this regard, the CFD model was used to screen various baffle designs. Suitable baffles provide a combination of good cell aeration and low shear stress.

Example baffles have a V-shape, a sidewall angle of 80°-110° and, in embodiments, a height when measured parallel to the longitudinal axis of the 5-liter vessel that is below the 2.5-liter fill level. In embodiments, the baffle height can range from 60% to 120% of the fill level height.

The baffles extend along the vessel sidewall and, where the sidewall meets the vessel bottom wall, extend radially inward toward the vessel central axis. The degree to which the baffle extends inward into the bottom wall of the vessel can be measured by the angle formed between the baffle wall and the bottom wall of the vessel.

Shown in FIG. 10 are contour plots of the air volume fraction in (a) a 3-liter baffled vessel, (b) a 5-liter baffled vessel using a baffle design from the 3-liter vessel, and (c) a 5-liter baffled vessel according to embodiments of the present disclosure.

Figure 10B:
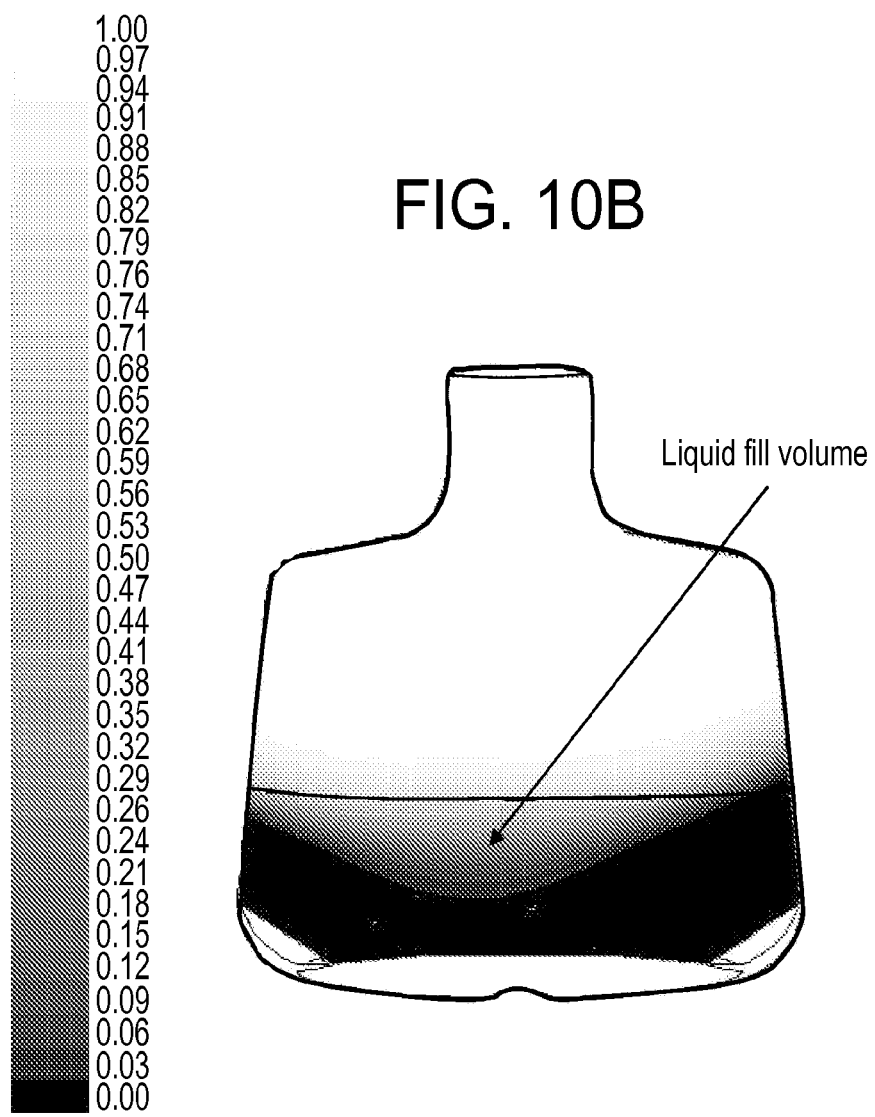
FIG. 10 is a modeled illustration of air volume fraction contours in (a) a 3-liter baffled vessel, (b) a 5-liter vessel with 3-liter baffles, and (c) a 5-liter vessel with baffles as disclosed in various embodiments.
Figure 10C:
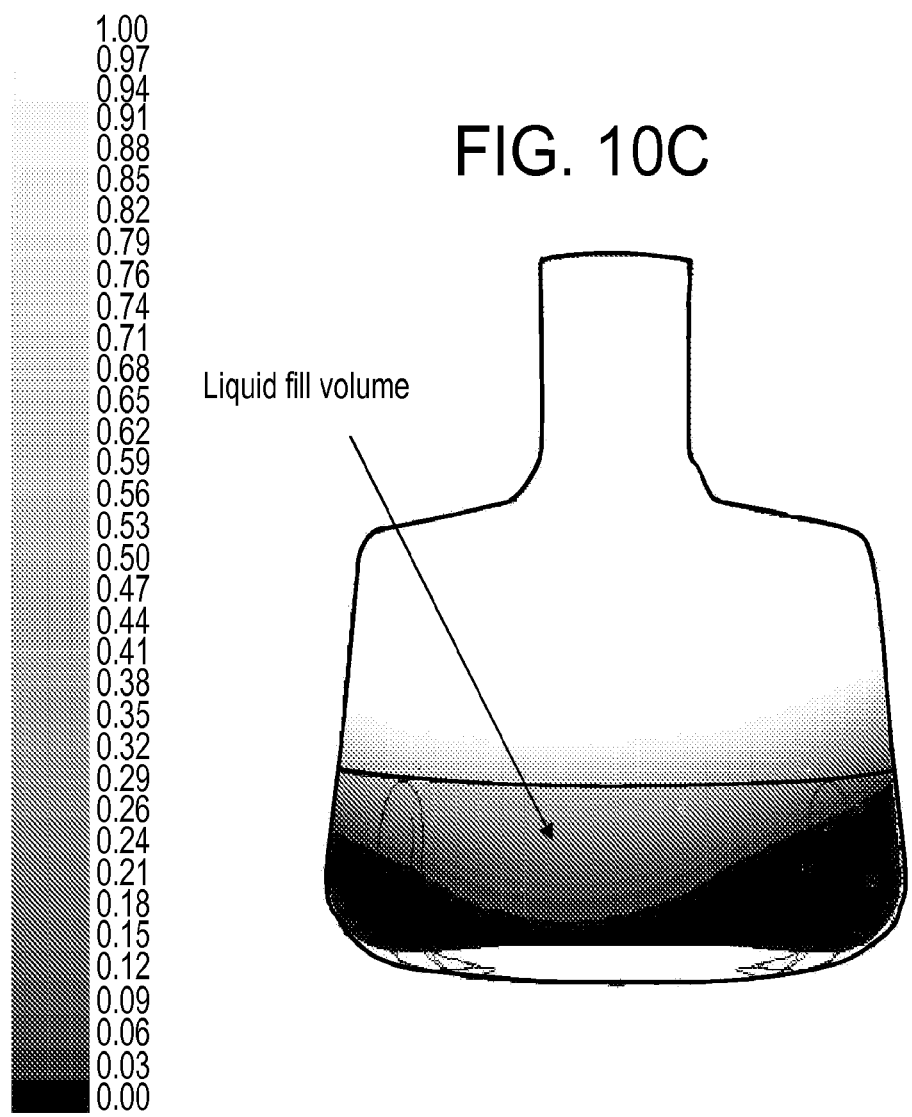

A comparison of FIGS. 10*b* and 10*c* shows that with the disclosed baffles, air entrains deeper into the liquid fill volume and therefore produces better cell aeration. This is also demonstrated by the volume-weighted average value of the air volume fraction as shown graphically in FIG. 11. From FIG. 11, which shows data for vessels agitated at 60 rpm, a 25% improvement in cell aeration is achieved with the 5-liter scaled-up vessel using the disclosed baffle design as compared to the 5-liter vessel with baffles from the 3-liter vessel.

Figure 11:
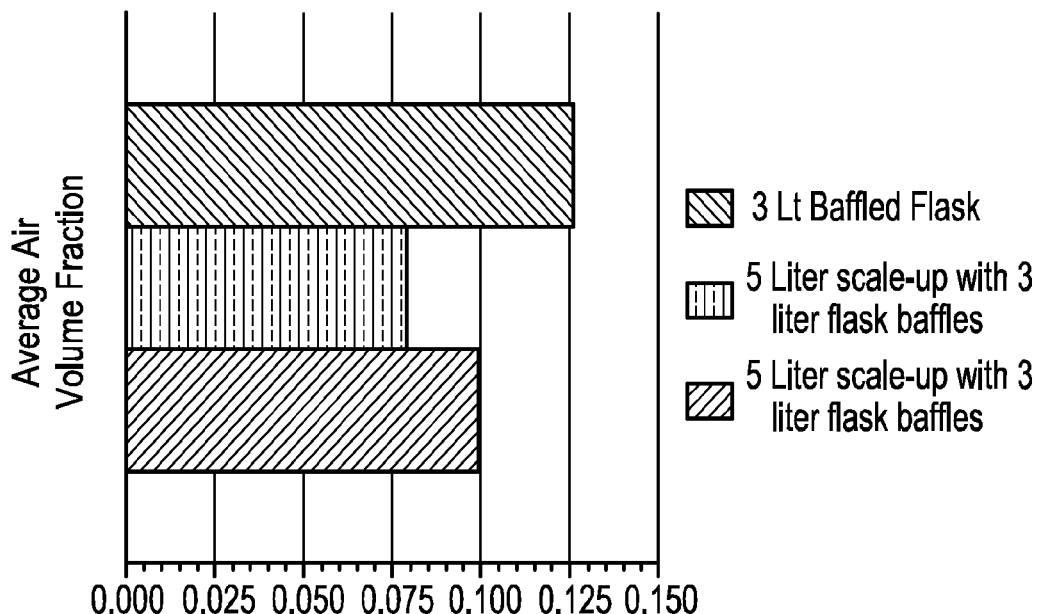
FIG. 11 is a graph showing the volume-weighted average air volume fraction for the vessels of FIG. 10.
Figure 12:
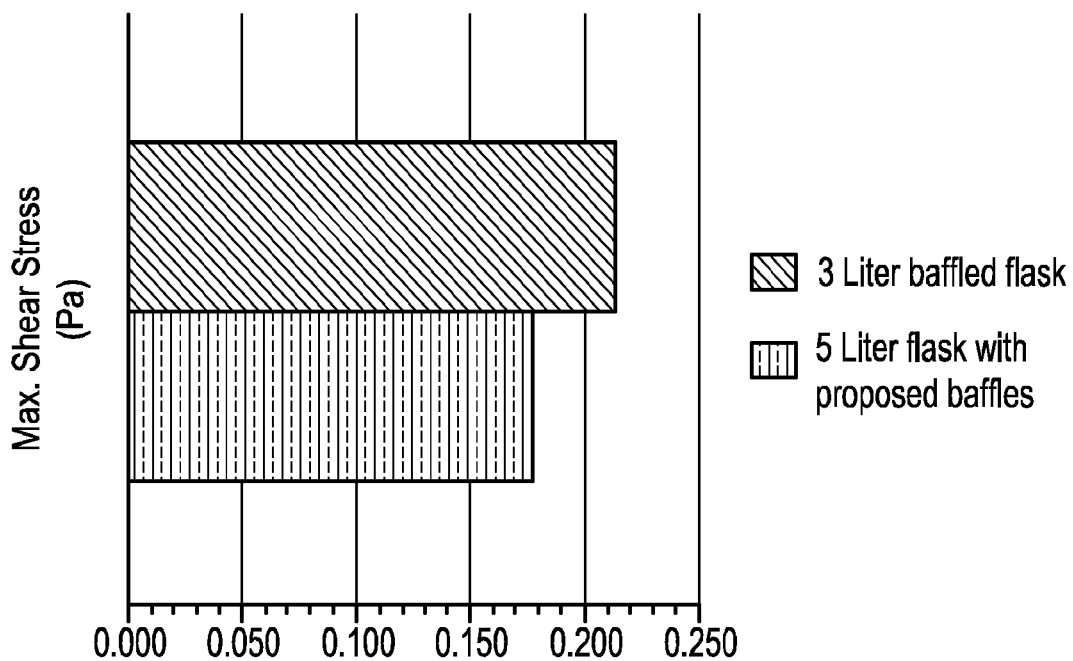
FIG. 12 is a graph showing maximum shear stress in 3-liter and 5-liter baffled vessels.
Figure 13B:
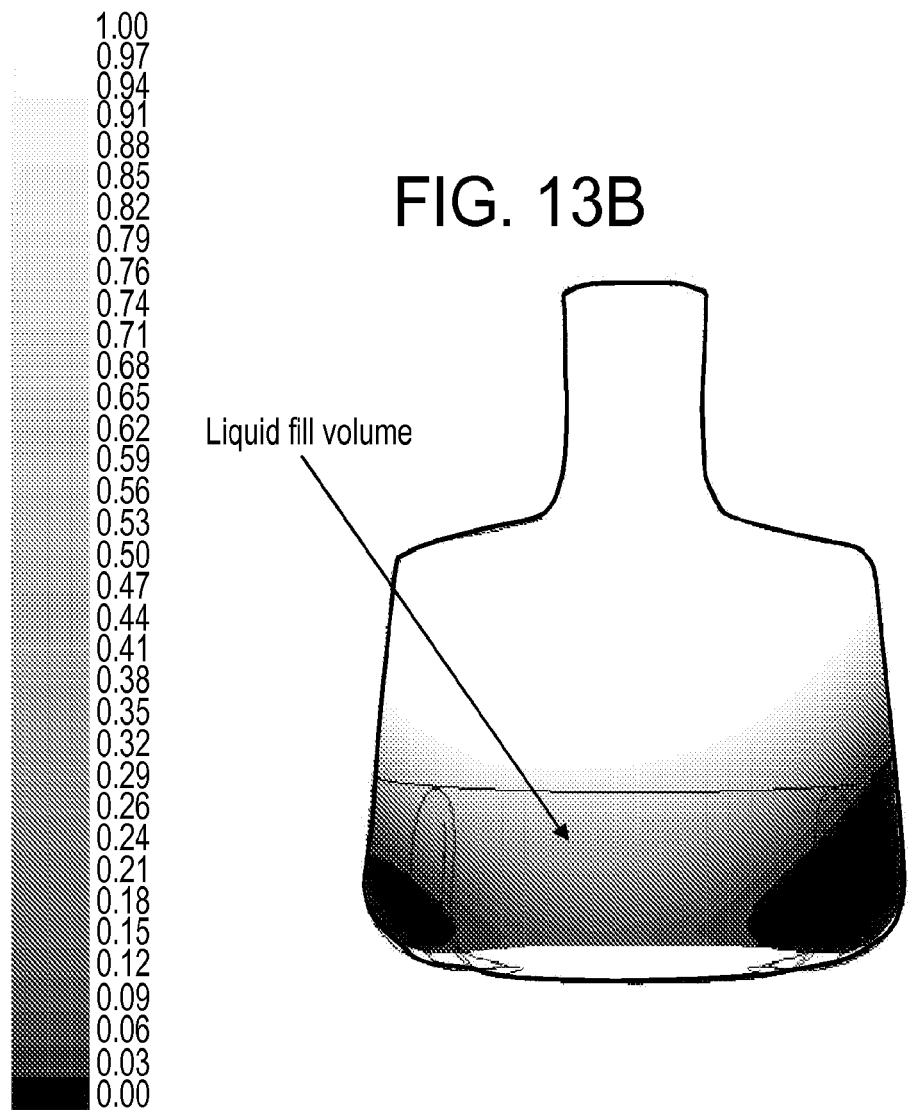

Referring still to FIG. 11, although the aeration performance of the 5-liter vessel is improved with the redesign of the baffles, it is still below the performance of the 3-liter baffled vessel. However, as shown in FIG. 12, for 60 rpm agitation the maximum shear stress of the 5-liter with the redesigned baffle is 16% less than the maximum shear stress in its 3-liter counterpart. Data from FIG. 12 suggest that it may be possible to increase cell aeration performance of the 5-liter baffled vessel by agitating it at higher frequency, i.e., greater than 60 rpm. The CFD model shows a significant increase in cell aeration when the 5-liter baffled vessel is agitated at 90 rpm. This is demonstrated in FIG. 13, which shows air volume contours in an example 5-liter vessel at (a) 60 rpm and (b) 90 rpm.

Figure 14:
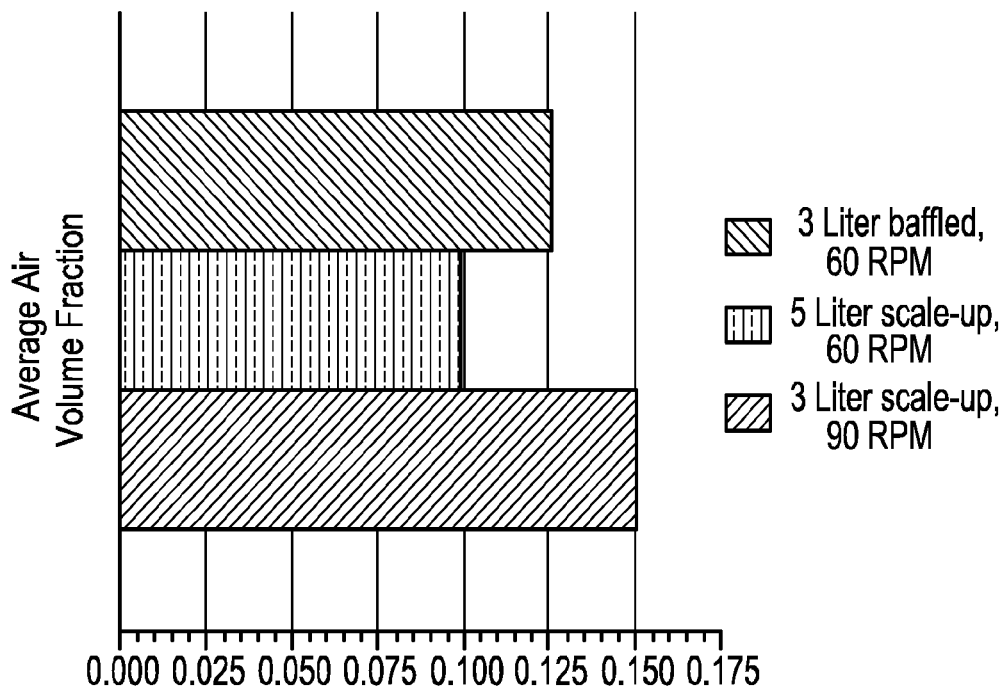
FIG. 14 is a graph showing average air volume fraction in 3-liter and 5-liter baffled vessels.
Figure 15:
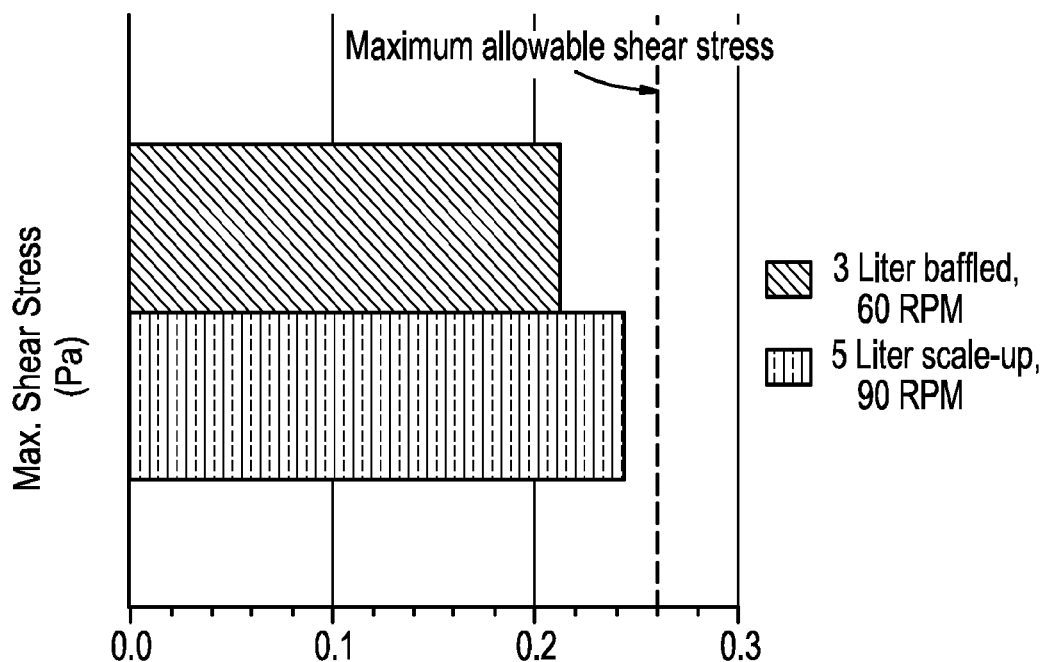
FIG. 15 is a graph showing maximum shear stress in 3-liter and 5-liter baffled vessels.

Referring to FIG. 14, when agitated at 90 rpm, the disclosed 5-liter scaled-up bioreactor provides a 19% increase in cell aeration over its 3-liter counterpart. This is made possible by the redesigned baffles, which help reduce the maximum shear stress so that even when the 5-liter baffled vessel is agitated at 90 rpm, the maximum shear stress is 0.24 Pa, which is only 15% greater than the shear stress for the 3-liter baffled vessel and less than the maximum allowable shear stress (0.28 Pa). This result is shown graphically in FIG. 15.

While the 5-liter baffled vessel is described herein as having four baffles, the CFD model shows that it is possible to use 2 to 6 baffles and still improve the growth rate of biological media. In embodiments, the plurality of baffles is evenly-spaced around the bottom of the vessel.

In embodiments, the 5-liter bioreactor vessel is made from (or internally-coated with) a hydrophilic material, which promotes liquid crawl higher up the vessel sidewalls, leaving more space in the center of the liquid fill volume for air to entrain and therefore increase cell aeration. Optionally, an inner surface of the vessel may be treated to form a hydrophilic inner surface. Example surface treatments include Corning's CellBIND® surface treatment and tissue culture treatments such as exposure to a corona discharge. The vessel, in further embodiments, is a unitary part that may be formed, for example, by injection molding or blow molding. The vessel is free of any joining seams. Example vessel materials include polycarbonate, polypropylene and polyethylene. The vessel may include a single chamber.

Figure 16A:
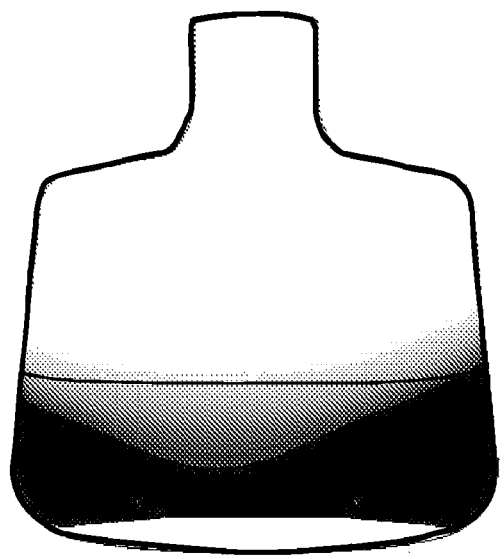
FIG. 16 is a modeled illustration showing the effect of vessel wall material on aeration.
Figure 16B:
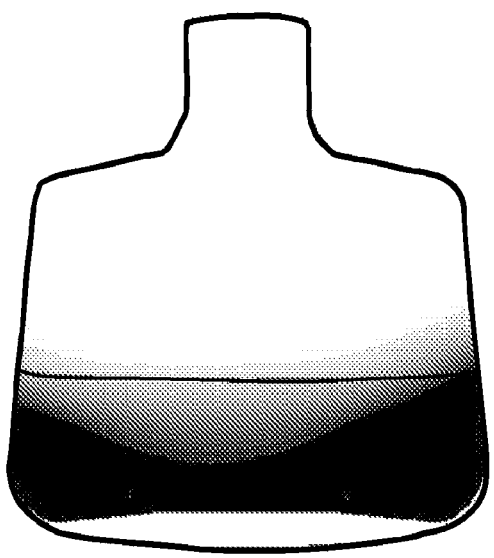

The effect of the bioreactor vessel material on aeration is illustrated in FIG. 16. CFD analysis shows that when the vessel material is changed from hydrophobic (e.g., liquid contact angle=30°) to hydrophilic (e.g., liquid contact angle=90°) a 13% improvement to the volume-weighted average air volume fraction is achieved. The average aeration for the hydrophobic inner vessel wall material was 0.0785, while the average aeration for the hydrophilic inner vessel wall material was 0.0888.

The 5-liter vessels disclosed herein may comprise a sidewall that terminates onto a nearly horizontal surface (i.e., parallel to the vessel bottom), which then transitions to a smaller diameter neck. The neck transitions to a larger diameter, optionally-threaded, outlet. In further embodiments, as illustrated in FIGS. 17A and 17B, the neck comprises a trough 300 that facilitates smooth pouring of the vessel's liquid contents. The trough neck also simplifies the evacuation of small amounts of fluid from the nearly horizontal interior transition surface 240.

In embodiments the trough 300 extends from the vessel sidewall 235 to the neck 210. The trough decreases from about 80° (e.g., 79°) to about 45° beyond horizontal the vessel tilt angle required to pour the complete liquid contents from the vessel.

The V-shaped trough connects a substantially vertical sidewall 235 to a vertical, smaller diameter pouring spout 260 that is concentric with the larger diameter of the vessel. A transition between the larger diameter of the vessel and the pouring spout is a slightly pitched horizontal surface 244. The addition of the trough minimizes splashing of the fluid stream exiting the vessel and also helps to eliminate any residual fluid that is difficult to decant from the vessel.

In an evaluation (2.5 liter fill volume, 90 rpm stir rate) comparing cell (Sf9) yield in a baffled 5-liter vessel according to embodiments with a commercially-available Thomson 5-liter Optimum Growth Flask, the total number of cells after 4 days of growth in the baffled 5-liter vessel was about $2.6 \times 10^{10}$ compared to only about $2 \times 10^{10}$ in the comparative vessel, which represents an increase in cell yield of about 30%.

Figure 18:
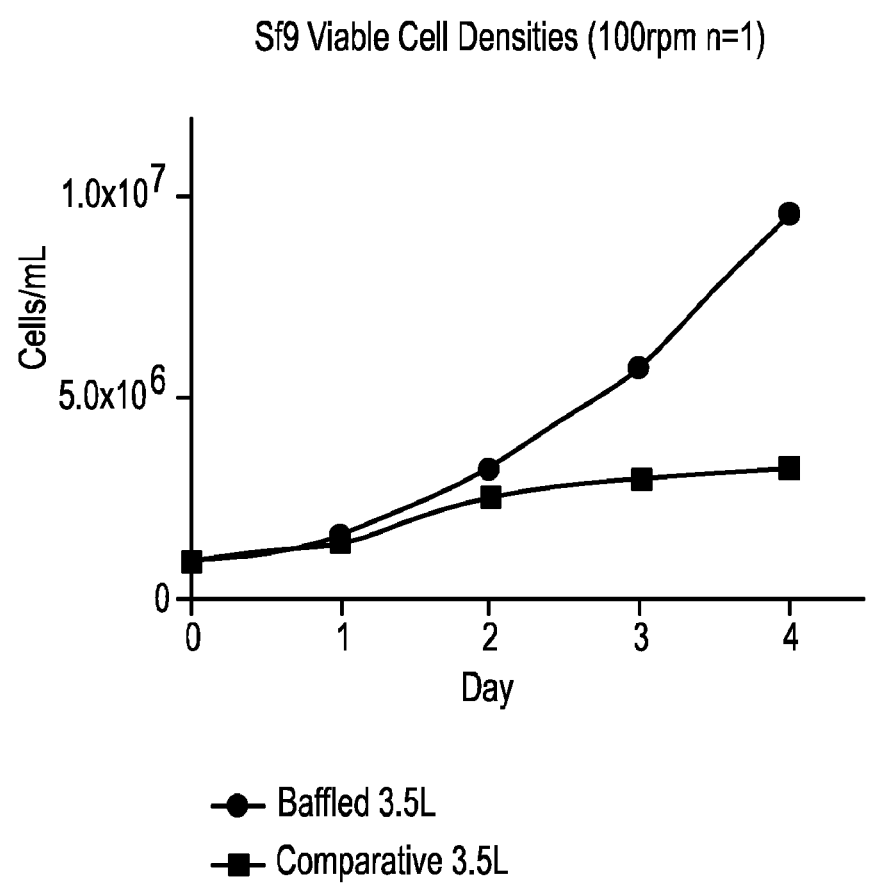
FIG. 18 is a plot comparing cell density versus time for a 5-liter baffled vessel with a commercially-available vessel.

In a related evaluation (3.5 liter fill volume, 100 rpm stir rate), a 300% increase in cell yield was observed after 4 days of growth, which demonstrates that the differentiation between the two flasks increases with increased fill volume. FIG. 18 is a plot comparing cell density versus time for the 5-liter baffled vessel with the commercially-available vessel.

The 5-liter bioreactor vessel disclosed herein has the same maximum diameter, height and shaking diameter as a 3-liter vessel and thus is advantageously compatible with existing infrastructure. With the larger overall volume, the 5-liter vessel enables a 67% increase in the volume of biological media that can be cultivated in the vessel. Moreover, when agitated at 1.5× the shaking frequency of the 3-liter bioreactor (i.e., 90 rpm versus 60 rpm), the 5-liter vessel achieves a 19% increase in cell aeration without exceeding the maximum shear stress limit for cell viability As used herein, the singular forms "a," "an" and "the" include plural referents unless the context clearly dictates otherwise. Thus, for example, reference to a "baffle" includes examples having two or more such "baffles" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a baffle comprising air and liquid biomedia include embodiments where a vessel consists of air and liquid biomedia and embodiments where a vessel consists essentially of air and liquid biomedia.

It will be apparent to those skilled in the art that various modifications and variations can be made to the present invention without departing from the spirit and scope of the invention. Since modifications, combinations, sub-combinations and variations of the disclosed embodiments incorporating the spirit and substance of the invention may occur to persons skilled in the art, the invention should be construed to include everything within the scope of the appended claims and their equivalents.

We claim:

1. A vessel for culturing cells comprising:
a vessel main body defined by a bottom having a rounded edge that is integral with a conically-shaped sidewall that tapers inward to a top surface;
two or more interior baffles configured to disrupt a liquid vortex of a liquid media contained within the vessel during agitation of the liquid media; and
an integral elongate annular neck extending upwardly from the top surface to a vessel opening, wherein
the neck is joined to the vessel main body via a tapered transition area, and
wherein the baffles extend along the conically-shaped sidewall, along the rounded edge to the bottom, and radially inward along the bottom, the baffles each comprising a v-shaped cross-section defined by sidewalls separated by an angle of 80° to 110°, and wherein the baffles extend radially inward from and downward from the rounded edge to the bottom of the vessel at an angle between 5° and 30°.

2. The vessel according to claim 1, wherein the top surface is substantially horizontal.

3. The vessel according to claim 1, wherein the vessel main body has a volume of at least 5 liters.

4. The vessel according to claim 1, wherein the vessel comprises a unitary part.

5. The vessel according to claim 1, wherein the vessel has a hydrophilic inner surface.

6. The vessel according to claim 1, wherein the neck diameter is less than a diameter of the vessel opening.

7. The vessel according to claim 1, wherein the neck diameter is at least 30% of a maximum vessel diameter.

8. The vessel according to claim 1, where the baffles are raised with respect to an inner surface of the vessel.

9. The vessel according to claim 1, wherein the neck further comprises a pour trough.

10. The vessel according to claim 1, wherein the baffles extend radially inward from the rounded edge to the bottom of the vessel at an angle of about 15 degrees.

11. A method of cultivating cells, comprising:
introducing a culture medium into the vessel of claim 1;
introducing at least one selected cell line into the vessel; and
agitating the vessel at a frequency of greater than 60 rpm.

12. The method according to claim 11, wherein the frequency is about 90 rpm.

* * * * *

UNITED STATES PATENT AND TRADEMARK OFFICE
CERTIFICATE OF CORRECTION

PATENT NO. : 10,870,822 B2
APPLICATION NO. : 15/304313
DATED : December 22, 2020
INVENTOR(S) : David Alan Kenney et al.

It is certified that error appears in the above-identified patent and that said Letters Patent is hereby corrected as shown below:

On the Title Page

On page 2, in Column 2, item (56), OTHER PUBLICATIONS, Line 4, delete "Erienmeyer" and insert -- Erlenmeyer --, therefor.

On page 2, in Column 2, item (56), OTHER PUBLICATIONS, Line 13, delete "Aptent" and insert -- Patent --, therefor.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*